United States Patent [19]

LaBove et al.

[11] 4,087,864

[45] May 9, 1978

[54] DISPENSING VEST FOR PATIENTS RECEIVING HYPERALIMENTATION

[75] Inventors: Larry D. LaBove; Patrick A. Mann, both of Houston, Tex.

[73] Assignee: Larry D. LaBove, Houston, Tex.

[21] Appl. No.: 755,976

[22] Filed: Dec. 30, 1976

[51] Int. Cl.² .................... A41D 1/04; A61M 5/00
[52] U.S. Cl. ................................ 2/102; 128/214 R
[58] Field of Search ............... 2/102, 94, 96, 247, 2/249, 250, DIG. 7; 224/5 MC; 128/134, 214 R

[56] References Cited

U.S. PATENT DOCUMENTS

| 941,277 | 11/1909 | Schmidt | 224/5 K |
| 1,900,129 | 3/1933 | Ring | 2/102 |
| 2,678,447 | 5/1954 | Bracken | 2/94 |

Primary Examiner—Doris L. Troutman
Attorney, Agent, or Firm—Pravel, Wilson & Gambrell

[57] ABSTRACT

A vest is provided which patients undergoing intravenous hyperalimentation (total parenteral nutrition) treatment may wear, permitting the patients/recipients to move about and continue to receive intravenous nourishment. The vest is provided with pouches to receive bags of the hyperalimentation solution, a pocket to receive a pump to transfer the solution to the recipient's body and a pocket for a power supply for the pump. The vest permits hyperalimentation recipients who would otherwise be bed-ridden to lead a more normal and active life.

9 Claims, 4 Drawing Figures

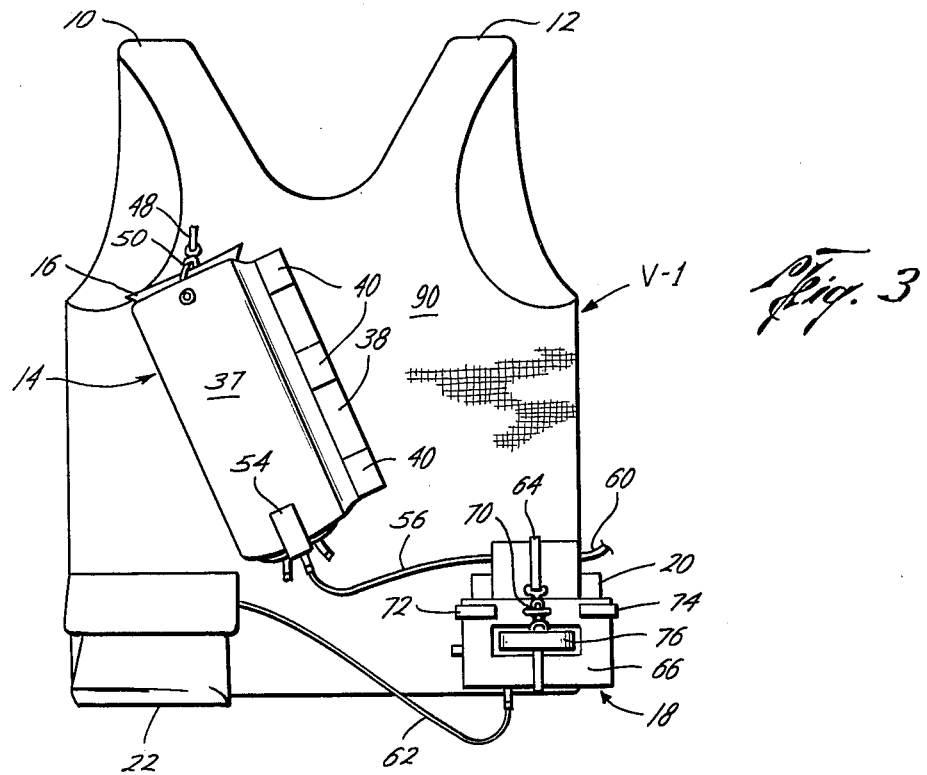
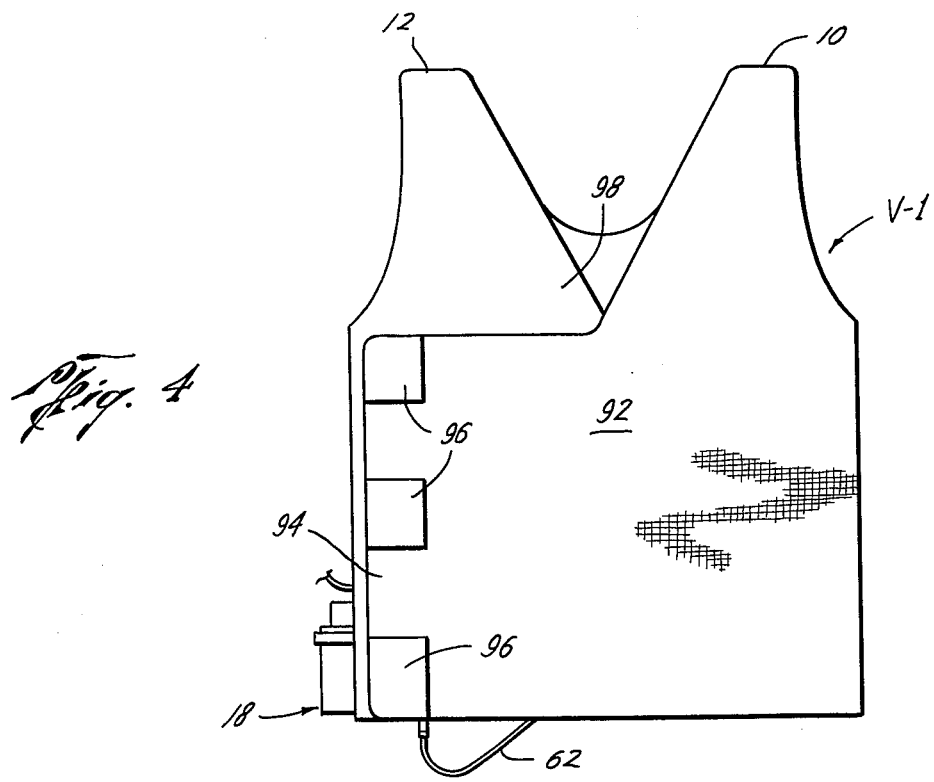

DISPENSING VEST FOR PATIENTS RECEIVING HYPERALIMENTATION

BACKGROUND OF THE INVENTION

1. FIELD OF INVENTION

The present invention relates to vests for patients receiving medication, namely intravenous hyperalimentation.

2. DESCRIPTION OF PRIOR ART

Continuous intravenous hyperalimentation is a technique which has been developed within the last ten years for persons who cannot absorb adequate nutrients from their digestive systems to sustain their bodies. Typical reasons for this might include intestinal surgery or adverse reactions to chemotherapy in cancer treatment.

However, as far as is known, prior intravenous hyperalimentation has, due to the continuous nature of treatment required, forced the patient to remain continuously in a hospital to receive treatment. This has caused dissatisfaction on the part of some patients who, other than for digestive problems requiring hyperalimentation, might otherwise be able to lead nearly normal lives. The possibility of adverse psychological reactions by these people to extended hospital stays has concerned some physicians.

SUMMARY OF THE INVENTION

Briefly, the present invention provides a new and improved vest for a patient receiving intravenous medication, particularly hyperalimentation solutions, which permits the patient to move about while receiving the medication. If the patient is otherwise in suitable health, outpatient status may be achieved by the patient, who may then return at suitable time intervals for replenishment of the medication, and inspection and maintenance of the pump and power supply.

The vest includes a body attachment harness for mounting on the patient's upper body which has a medication pocket mounted therewith for receiving a bag of the medication for the patient. A pump pocket is also mounted with the harness to receive a pump which transfers medication from the bag to the patient via suitable tubes, typically intravenously to the patient's subclavian vein. A power supply pocket is also mounted with the harness to receive a power supply which operates the pump.

Accordingly, when the appropriate medication and equipment are placed in their respective pockets, the patient may don the harness and move about without being required to stay in one location while receiving intravenous medication. In certain situations, the patient may be granted outpatient status, returning periodically, typically daily for replenishment of medication, usually by receiving new medication bags. When necessary, hospital personnel may also monitor the status of the pump and power supply as well.

BRIEF DESCRIPTION OF THE DRAWINGS

FIGS. 3 and 4 are front and back views, respectively, of another embodiment of a vest according to the present invention.

DESCRIPTION OF THE PREFERRED EMBODIMENT

Figure 1:
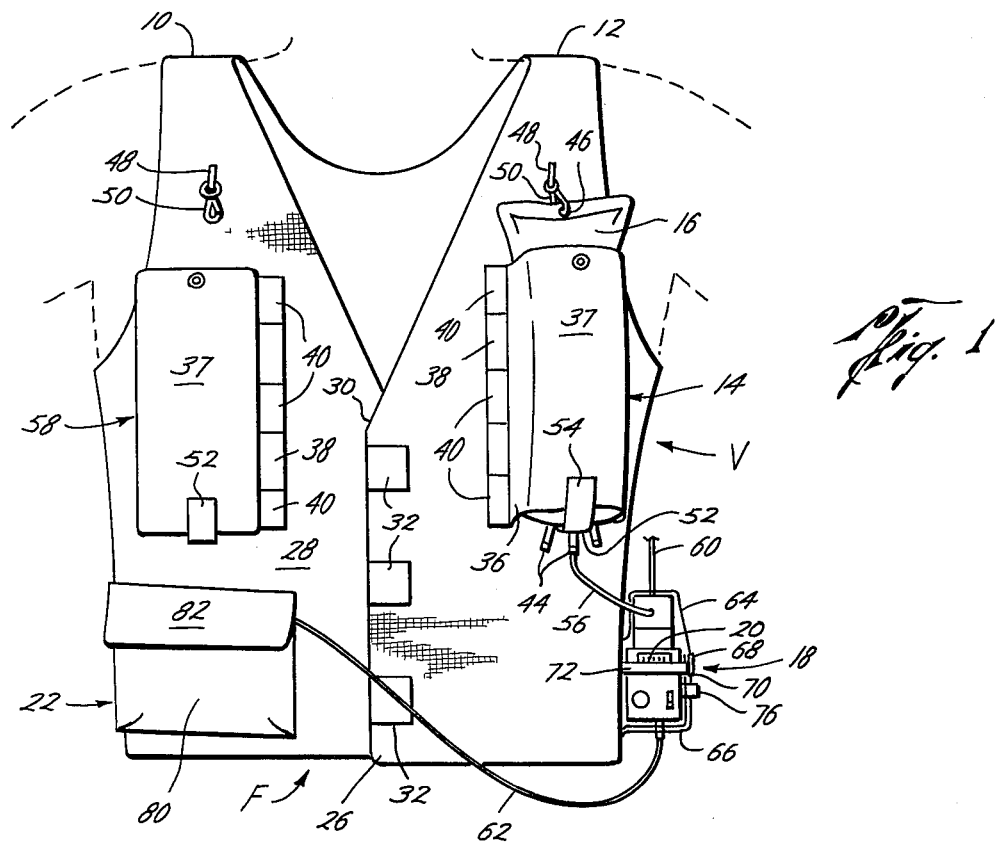
FIGS. 1 and 2 are front and back views, respectively, of a vest according to the present invention.

In the drawings, the letter V designates a vest according to the present invention for a patient receiving intravenous medication, particularly hyperalimentation solutions. Due to the nature of the treatment required, the patient is often required to receive continuous supplies of the medication solution over an extended period of time. Previously, such patients were required to remain in the hospital and stay substantially immobile while receiving such treatment.

The vest V is made of a suitable cloth or synthetic fabric. Preferably, denim or an equivalent fabric is used due to strength and long wear afforded by this type of fabric. The vest V typically covers the upper torso of the patient extending to approximately the waist of the patient, as indicated by the phantom lines (FIG. 1).

Figure 2:
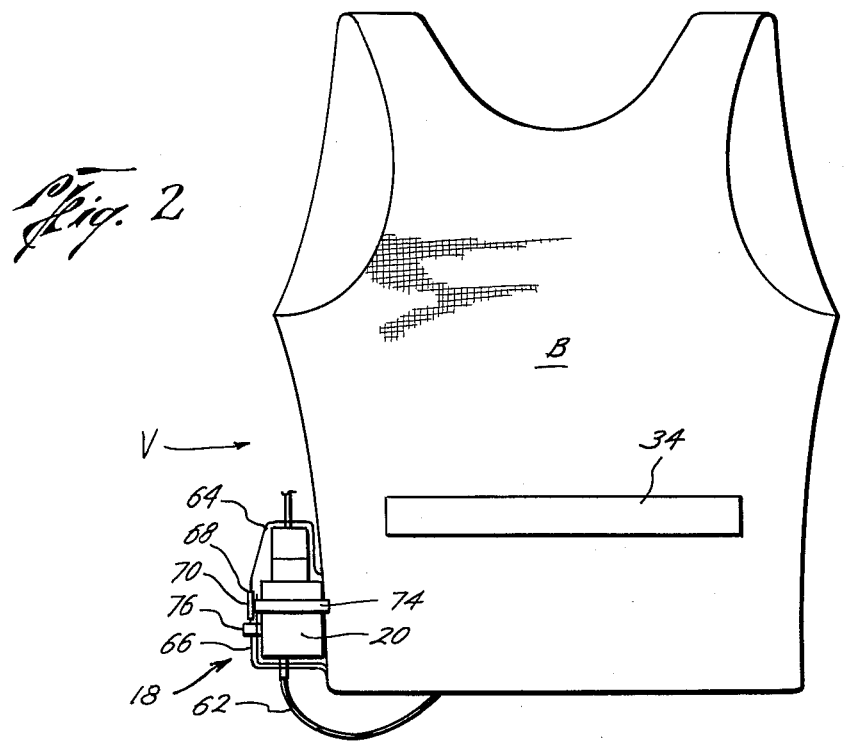

Considering the vest V more in detail, such vest is in the general form of an enclosing body harness having shoulder straps 10 and 12 for suspending the body harness about the body of the patient. The vest V further includes a front panel F (FIG. 1) and a body panel B (FIG. 2) for surrounding the body of the patient. A medication pocket 14 is formed at a suitable location on the front panel F, such as in the vicinity of the patient's chest, and receives therein a bag 16 of medication to be intravenously furnished to the patient. A pump pocket 18 is mounted with the vest V and receives therein a pump 20 which transfers medication from the bag 16 to the patient. Finally, a power supply pocket 22 is mounted with the vest V and contains therein a suitable power supply to operate pump 20.

In the vest V, the front panel F is formed from a left front panel 24 extending forwardly from the back panel B to a front closure 26 and a right front panel 28 extending forwardly from the back panel B to a front closure 30. Suitable openings are provided in panels 24 and 28 beneath straps 10 and 12 for passage of the patient's arms therethrough.

The front closures 26 and 30 each have suitable fasteners formed, as indicated at 32, to connect the left front panel 24 and the right front panel 28 together and enclose the upper torso of the patient within the vest V. The fasteners 32 may, for example, be formed from those synthetic materials which adhere when pressed together, sold under the trademark "VELCRO". However, it should be understood that buttons, snaps or other suitable clothing fasteners may be used for the fasteners 32, if desired. For fitting purposes and comfort in wearing, a resilient or elastic waistband 36 may be included in the back panel B, where desired. Similar suitable waistbands may also be included in the front panel F to insure that the vest V is appropriately fitted to the patient's body for comfort in wearing.

Considering now the medication pocket 14 of the vest V more in detail, a flap 37 of suitable fabric is mounted with the left front panel 24 along one edge of such flap. An end portion 38 of the flap has a set of fasteners 40 formed therealong which are adapted to engage a matching set of fasteners formed on the left front panel 24.

The flap 37 of the medication pocket 14 is of a sufficient length to form an U-shaped sleeve, extending outwardly from the front panel 24, of a size adequate to retain therein the medication bag or pouch 16, which is a conventional intravenous solution bag or pouch. As is typical, such pouch includes several outlets 42 at a lower end thereof and extending downwardly therefrom, as well as a hanging loop 46 formed at an upper end thereof.

An attaching tab 48 having a snap ring 50 formed at a lower end thereof is mounted with the panel 24 above the medication pocket 14 to retain the pouch 16 in the proper position on the vest V. A support strap 52 is mounted with the panel 24 beneath the flap 35 and has a fastener formed at an outer end 54 thereof to engage a co-acting fastener on the flap 37 and retain the pouch 16 within the sleeve formed by the flap 37. Preferably, an opening or grommet is formed on the lower strap 52 to permit an appropriate outlet 44 of the pouch 16 to pass therethrough for connection with a tube or conduit 56 which connects the pouch 16 with the pump 20.

For certain patients, the amounts of hyperalimentation solution required during the time interval between visits may be greater than the contents of one bag or pouch 16. Accordingly, the vest V is provided with a second medication pocket 58 on the right front panel 28 of the vest V which receives an additional medication pouch 16, as needed. The second medication pocket 58 is of like construction and function to the pocket 14 and accordingly components thereof, as well as structure of the vest V co-acting therewith, bear like reference numerals to the first pocket 14.

The pump pocket 18 of the vest V contains therein a suitable, conventional medication dispensing pump 20, as has been set forth. One such pump is the Model 911 pump manufactured by Extracorporeal Medical Specialties, Inc. of King of Prussia, PA. The pump 20 is connected to the medication pouch 16 by the tube 56, as has been set forth, and moves the medication solution from the conduit 56 through a conduit 60 to a suitable intravenous feeding needle, usually located in the subclavian vein of the patient. The pump P receives operating power via a conductor 62 from a suitable power supply in the power supply pocket 22. Considering the pump pocket 18 (FIGS. 1 and 2) more in detail, a lower pocket flap 64 and an upper pocket flap 66 are mounted with the body harness of the vest V at a suitable location such as the lower left side, as shown. The pocket flaps 64 and 66 fold over and enclose the pump 20 therein and are interconnected by an upper clasp 68 and a lower clasp 70 or other suitable fastening means. A front side strap 72 (FIG. 1) and a rear side strap 74 (FIG. 2) extend outwardly from connections with the vest V and are fastened with the pocket flap 66 by suitable fasteners to form side barriers for the pump 20 in the pocket 18. In the embodiment shown, an opening is formed in the lower pocket flap 66 for a carrying strap 76 of the pump 20 to extend therethrough and the lower clasp 70 passes through such strap to further assist in retaining the pump 20 in the pocket 18.

The power supply pocket 22 contains a suitable power supply, typically a set of dry cell batteries, to provide electrical operating power to the pump 20. The power supply pocket 22 includes a lower three-sided pouch or pocket member 80 attached at a suitable location on the vest V, such as the lower portion of the right front panel 28. A covering flap 82 is attached to the vest V above the pouch 80 and folds downwardly to enclose and cover the power supply within the pocket 22. Suitable fasteners are provided to permit closing of the pocket 22 to protect the power supply contained therein.

It should be understood that numerous modifications to the foregoing embodiment of the vest V of the present invention may be made. For example, the location of the power supply pocket 22 and the pump pocket 18 may be interchanged on the vest V, and may be adjusted to various locations on either of the front panels 24 and 28, as desired for patient comfort. The pockets of the vest V could be located on the back panel, but front panel mounting has been found more desirable to permit the patient to make adjustments while wearing the vest V. Further, different configurations and locations of medication pockets may be used, if desired.

For example, in an alternate vest V-1 (FIGS. 3 and 4), the body harness includes a front panel 90 and a back panel 92 joined at the right side of the torso of the patient. The back panel 92 has a side closure 94 formed thereon with fasteners 96 attached thereto. The front closure 90 includes an inner extension 98 extending inwardly behind the patient's back from a side closure thereof with fasteners which coact with the fasteners 96 of the back panel 92 so that the vest V is securely fastened about the upper torso of the patient.

With the exception of the location of the medication pocket 14, the pump pocket 18 and the power supply pocket 22, the remaining structure of the vest V-1 is of like structure and function to the vest V and, accordingly, like reference numerals are applied.

In the use of the present invention, the patient reports, either as an in- or out-patient and receives the prescribed number of bags 16 of hyperalimentation solution which are inserted in the pockets 14, and one of such bags 16 is connected through the conduit 56 to the pump 20. If necessary, at this time, maintenance and adjustments may be made to the pump 20 and to the power supply in the power supply pocket 22. Where necessary, the previous vest V may be returned for laundering and replaced with a new, clean vest.

After receiving the medication in the vest V, the patient may, if in out-patient status, return home while receiving the medication. Should the medication bag or pouch leak or become damaged, the patient may switch to the other medication pouch or return to receive a replacement. If the patient is required to remain hospitalized, but health conditions permit, movement about the hospital for exercise or similar reasons is permitted, while the patient receives medication.

Accordingly, from the foregoing, it can be seen that a patient using the vest V of the present invention may receive intravenous medication for an extended period of time, while being permitted to move about, even as an outpatient from a hospital, while receiving the medication. The patient merely dons the vest V of the present invention and is thereby permitted to move about without being required to stay in one location while receiving such medication. Thus, the patient may receive the needed medical treatment without suffering adverse psychological effects of being required to remain virtually immobile and stay within the confines of a hospital while receiving the requisite medical treatment.

The foregoing disclosure and description of the invention are illustrative and explanatory thereof and various changes in the size, shape and material as well as in the illustrated construction of the preferred embodiment may be made without departing from the spirit of the invention.

We claim:

1. A vest for a patient receiving intravenous medication to permit the patient to move about while receiving the medication, comprising:

(a) a body attachment harness for mounting on the patient's upper body, said body harness having fastener means formed thereon;
(b) a medication pocket mounted with said harness adjacent said fastener means for receiving a bag having a suspending ring and containing intravenous hyperalimentation medication, which medication is to be intravenously furnished to the patient, said medication pocket comprising:
(1) a flap of material mounted along a side edge thereof, and extending outwardly from, said body harness;
(2) fastener means mounted with said flap at an end opposite said side edge to engage said fastener means of said body harness and thereby form said flap of material into a sleeve; and
(3) said sleeve being of a size to receive and retain therein the bag of intravenous hyperalimentation medication;
(c) a snap ring mounted with said body harness above said sleeve for attaching to the suspending ring of the bag of intravenous hyperalimentation medication to attach the bag to said body harness;
(d) a pump pocket mounted with said body harness for receiving a pump for transferring medication from the bag to the patient; and
(e) a power supply pocket mounted with said harness for receiving a power supply to provide operating power to the pump in the pump pocket, permitting the patient to don the harness when the bag of medication, pump and power supply are placed in their respective pockets and to move about while receiving the intravenous medication.

2. The structure of claim 1, further including at least one additional medication pocket mounted with said harness for receiving at least one additional bag of medication.

3. The structure of claim 1, wherein said body attachment harness includes:

(a) strap members for fitting over the shoulders of the patient;
(b) a front panel supported by said strap members for enclosing the front portion of the upper body of the patient; and
(c) a back panel supported by said strap members for enclosing the back portion of the upper body of the patient.

4. The structure of claim 3, wherein said front panel comprises:
(a) a left panel member extending forwardly from said back panel member to a front closure;
(b) a right front panel member extending forwardly from said back panel member to a front closure; and
(c) fastener means for connecting said left and right front panel members at the front closures thereof.

5. The structure of claim 3, wherein said front and back panels each have a side closure formed thereon adjoining the side closure of the other, and further including:
fastener means for connecting said front and back panels at the side closure thereof.

6. The structure of claim 1, further including:
resilient band means mounted with said body harness to cause the vest to conform to the body of the patient.

7. The structure of claim 1, wherein said medication pocket further includes:
a support strap mounted with said body harness beneath said flap to retain the medication bag in said sleeve of said medication pocket.

8. The vest of claim 7, wherein the bag of medication has an outlet extending downwardly therefrom, and wherein said support strap has an opening formed therein for passage of the outlet therethrough.

9. The vest of claim 8, wherein said sleeve has a fastener formed thereon and said support strap has a fastener formed at an outer end thereof to engage said fastener formed on said sleeve.

* * * * *